US007871431B2

(12) United States Patent
Gurm et al.

(10) Patent No.: US 7,871,431 B2
(45) Date of Patent: Jan. 18, 2011

(54) APPARATUS FOR TREATING ATHEROSCLEROSIS

(75) Inventors: Hitinder Gurm, Ann Arbor, MI (US); Jay Yadav, Hunting Valley, OH (US); Ji-Feng Chen, Lakewood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1421 days.

(21) Appl. No.: 11/188,347

(22) Filed: Jul. 25, 2005

(65) Prior Publication Data

US 2006/0025843 A1 Feb. 2, 2006

Related U.S. Application Data

(60) Provisional application No. 60/591,385, filed on Jul. 27, 2004.

(51) Int. Cl.
*A61F 2/06* (2006.01)

(52) U.S. Cl. .................................................... 623/1.11

(58) Field of Classification Search ................ 623/1.11, 623/1.35, 1.15; 604/103.07
See application file for complete search history.

(56) References Cited

U.S. PATENT DOCUMENTS 4,921,478 A * 5/1990 Solano et al. ............... 604/509
5,843,116 A 12/1998 Crocker et al.
6,039,721 A * 3/2000 Johnson et al. ............. 604/508
6,200,305 B1 * 3/2001 Berthiaume et al. ......... 604/509
6,494,905 B1 * 12/2002 Zedler et al. ............... 623/1.11
6,527,790 B2 * 3/2003 Chien et al. ................. 606/194
6,579,309 B1 * 6/2003 Loos et al. ................. 623/1.16
6,632,196 B1 * 10/2003 Houser .................... 604/96.01
6,761,734 B2 7/2004 Suhr
6,955,686 B2 10/2005 Majercak et al.
7,387,639 B2 * 6/2008 Bourang et al. ............ 623/1.11
7,476,243 B2 * 1/2009 Eidenschink ............... 623/1.11
7,753,951 B2 * 7/2010 Shaked et al. .............. 623/1.35
2002/0120325 A1 8/2002 Richter et al.
2002/0169494 A1 * 11/2002 Mertens et al. ............ 623/1.11
2002/0193873 A1 12/2002 Brucker et al.

(Continued)

FOREIGN PATENT DOCUMENTS

CA 2 360 551 A1 3/2000

(Continued)

*Primary Examiner*—Melanie Tyson
(74) *Attorney, Agent, or Firm*—Tarolli, Sundheim, Covell & Tummino LLP

(57) ABSTRACT

An apparatus for interventional treatment of atherosclerosis at a vascular bifurcation includes structure for receiving a first guidewire and a second guidewire. An exit for the second guidewire is located in a central section of the structure. A first balloon portion is secured to the structure so a proximal end is located adjacent the exit. A second balloon portion is secured to the structure so a distal end is located adjacent the exit on a side of the exit opposite the first balloon portion. An annular gap is defined between the proximal end of the first balloon portion and the distal end of the second balloon portion. The annular gap, at a radial outermost location relative to the structure, has a width that is equal to or less than a width of the annular gap at a radially innermost location relative to the structure. The apparatus also includes an expandable stent that is mountable about the first and second balloon portions.

17 Claims, 5 Drawing Sheets

U.S. PATENT DOCUMENTS

2004/0015231 A1* 1/2004 Suhr ........................ 623/1.35
2004/0039331 A1* 2/2004 Coppi et al. ........... 604/101.04
2004/0073285 A1 4/2004 Wilson et al.
2004/0138732 A1 7/2004 Suhr et al.
2004/0225345 A1 11/2004 Fischell et al.
2004/0249434 A1 12/2004 Andreas et al.
2005/0027344 A1 2/2005 Eidenschink
2005/0131524 A1 6/2005 Majercak et al.
2005/0288771 A1 12/2005 Majercak et al.

FOREIGN PATENT DOCUMENTS

WO WO 2005/014077 A2 2/2005

* cited by examiner

APPARATUS FOR TREATING ATHEROSCLEROSIS

RELATED APPLICATION

This application is related to U.S. Provisional Patent Application Ser. No. 60/591,385, filed Jul. 27, 2004, the subject matter of which is incorporated herein by reference.

TECHNICAL FIELD

The present invention relates to an apparatus for treating atherosclerosis, and is particularly directed to an apparatus for interventional treatment of atherosclerosis at a vascular bifurcation formed by a junction of a branch vessel with a main vessel.

BACKGROUND OF THE INVENTION

Balloon catheters are commonly used to treat certain conditions of a blood vessel, such as a partial or total occlusion or lesion of the vessel that may be caused by, for example, atherosclerotic plaque or thrombosis. In an angioplasty procedure, a guidewire is inserted into an occluded blood vessel. A balloon portion of a catheter is advanced over the guidewire to the site of the occlusion. When the balloon portion is properly positioned relative to the occlusion, the balloon portion is inflated. The inflating of the balloon portion of the catheter compresses the occlusion and thereby, restores normal blood flow through the blood vessel.

In some instances, a stent may be implanted in the blood vessel to help prevent the occlusion from recurring. It is common for a stent to be delivered to the site of an occlusion and deployed using a balloon catheter. In such a case, the stent, in an unexpanded condition, is mounted on the uninflated balloon portion of the catheter. When the stent is properly positioned relative to the occlusion, the balloon portion of the catheter is inflated. The inflating of the balloon portion of the catheter expands the stent in the blood vessel.

Difficulties often arise when treating an occlusion that occurs at or near a vascular bifurcation formed by an intersection of a main vessel with a branch vessel. A common method for treating such an occlusion involves implanting a first stent in the main vessel adjacent to the bifurcation. After the first stent is implanted in the main vessel, a second stent is implanted in the branch vessel at a location adjacent to the bifurcation. This procedure is often difficult and time consuming. One common difficulty that is encountered during this procedure involves threading a guidewire for the balloon catheter used to deliver the second stent through the struts of the implanted first stent. Another common difficulty arises when the implantation of the first stent causes plaque to close the branch vessel at the location of the bifurcation. When the branch vessel becomes closed, insertion of the guidewire into the branch vessel is extremely difficult.

Prior to placement of one or more stents in a blood vessel, it is common for the occlusion to be pre-dilated using a balloon angioplasty procedure. In preparation for a balloon angioplasty procedure at a vascular bifurcation, a first guidewire is inserted into the main vessel and a second guidewire is inserted into the branch vessel. FIG. 7 illustrates a vascular bifurcation 110 in which first and second guidewires 112 and 114, respectively, are located. As FIG. 7 illustrates, the first guidewire 112 extends through the main vessel 116 past the junction of the branch vessel 118. The second guidewire 114 extends through the main vessel 116 to the branch vessel 118 and then extends into the branch vessel.

FIG. 7 also illustrates an occlusion 120 (a deposit of plaque) at the bifurcation. It should be noted that the occlusion 120, which may be caused by a stenosis or restenosis in the blood vessel, may be located in the main vessel upstream of the branch vessel, in the main vessel downstream of the branch vessel, at the intersection of the main vessel and the branch vessel, in the branch vessel downstream of the main vessel, or in a combination of any of these locations.

When the first and second guidewires 112 and 114 are inserted prior to the balloon angioplasty procedure, the second guidewire enables access to the branch vessel even if shifting plaque closes off the branch vessel during the balloon angioplasty procedure. In most known stenting procedures for treating occlusions at vascular bifurcations, however, the second guidewire must be withdrawn from the branch vessel prior to a stent being implanted in the main vessel so that the second guidewire will not interfere with the deployment of the stent in the main vessel. Consequently, difficulty may be experienced in re-inserting the second guidewire into the branch vessel.

FIG. 8 illustrates a segmented balloon catheter 130 disclosed in U.S. Pat. No. 6,761,734. The segmented balloon catheter 130 of FIG. 8 includes a single shaft 132 upon which first and second balloon portions 134 and 136, respectively, are mounted. A longitudinal passageway 138 extends through the shaft 132. A transverse port 142 extends through the shaft 132 at a location between the first and second balloon portions 134 and 136. The segmented balloon catheter 130 of FIG. 8 enables a first guide wire 146, which is pre-positioned in a main vessel 148, to be inserted into the shaft 132 and threaded through the longitudinal passageway 138 and out of an opposite end of the shaft. The segmented balloon catheter 130 also enables a second guide wire 152, which is pre-positioned in a branch vessel 154, to be inserted into the transverse port 142 and threaded through the longitudinal passageway 138 and out of an end of the shaft 132. The segmented balloon catheter 130 is useful for delivering and implanting a stent 158 in the main vessel 148.

One problem arising from the use of the segmented balloon catheter 130 of FIG. 8 results from the shape of the first and second balloon portions 134 and 136 adjacent the transverse port 142. As FIG. 8 illustrates, adjacent ends of the first and second balloon portions 134 and 136 are generally frustoconical and taper away from one another. As a result, a gap 160 located between the first and second balloon portions 134 and 136 is quite large relative to an axial length of the segmented balloon catheter 130. For example, a twenty millimeter long segmented balloon catheter 130 may have up to five millimeters between the first and second balloon portions 134 and 136 at the gap 160. This large gap 160 at the center of the segmented balloon catheter 130 may result in a non-uniform stent deployment. Specifically, the central portion of stent 158 may not be expanded to the same diameter as the proximal and distal ends of the stent, as FIG. 8 illustrates.

SUMMARY OF THE INVENTION

The present invention relates to an apparatus for interventional treatment of atherosclerosis at a vascular bifurcation formed by a junction of a branch vessel and a main vessel. The apparatus comprises structure for receiving a first guidewire positioned in the main vessel and a second guidewire positioned in the branch vessel. An exit for the second guidewire is located in a central section of the structure. A first balloon portion is secured to the structure so a proximal end is located adjacent the exit. A second balloon portion is secured to the structure so a distal end is located adjacent the exit on a side opposite the first balloon portion. An annular gap is defined between the proximal end of the first balloon portion and the distal end of the second balloon portion. The annular gap, at a radial outermost location relative to the structure, has a width that is equal to or less than a width of the annular gap at a radially innermost location relative to the structure. The second guidewire is extendable through the annular gap. The apparatus also comprises an expandable stent that is mountable about the first and second balloon portions and is expandable by the first and second balloon portions into engagement with the main vessel at the vascular bifurcation.

According to another aspect, the present invention relates to an apparatus for interventional treatment of atherosclerosis at a vascular bifurcation formed by a junction of a branch vessel and a main vessel. The apparatus comprises structure for receiving a first guidewire positioned in the main vessel and a second guidewire positioned in the branch vessel. An exit for the second guidewire is located in a central section of the structure. A first balloon portion is secured to the structure so a proximal end is located adjacent the exit. The proximal end of the first balloon portion has an arcuate end surface. A second balloon portion is secured to the structure so a distal end is located adjacent the exit on a side opposite the first balloon portion. The distal end of the second balloon portion also has an arcuate end surface. The arcuate end surfaces of the first and second balloon portions extend toward one another and define an annular gap therebetween through which the second guidewire is extendable. The apparatus also comprises an expandable stent that is mountable about the first and second balloon portions and is expandable by the first and second balloon portions into engagement with the main vessel at the vascular bifurcation.

According to a further aspect, the present invention relates to an apparatus for interventional treatment of atherosclerosis at a vascular bifurcation formed by a junction of a branch vessel with a main vessel. The apparatus comprises at least one shaft having oppositely disposed proximal and distal ends and a central section between the ends. The at least one shaft includes at least one channel extending through the at least one shaft. The at least one channel is for receiving a first guidewire placed into the main vessel and a second guidewire placed into the branch vessel. The at least one channel includes means for allowing the second guidewire to exit the at least one channel in the central section of the at least one shaft. A first balloon portion has oppositely disposed first and second ends. The first end of the first balloon portion is secured to the distal end of the at least one shaft and the second end is secured to the central section of the at least one shaft. The second end of the first balloon portion has a toroidal shape defined by an arcuate end surface that curves outwardly from an inner diametrical surface of the first balloon portion to an outer diametrical surface. A second balloon portion has oppositely disposed first and second ends. The first end of the second balloon portion is secured to the proximal end of the at least one shaft and the second end is secured to the central section of the at least one shaft. The second end of the second balloon portion has a toroidal shape defined by an arcuate end surface that curves outwardly from an inner diametrical surface of the second balloon portion to an outer diametrical surface. The arcuate end surfaces of the first and second balloon portions face each other and define an annular gap between the second ends of the first and second balloon portions through which the second guidewire is extendable. The arcuate end surfaces function to minimize the axial length of the gap. An expandable stent is disposed about the first and second balloon portions for expansion by the balloon portions into engagement with the main vessel at the bifurcation to help prevent atherosclerosis. The second guidewire is extendable radially outward through the stent to provide access for additional intervention in the branch vessel as needed.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

The present invention relates to an apparatus 10 (FIG. 2) for treating atherosclerosis, and is particularly directed to an apparatus 10 for interventional treatment of atherosclerosis at a vascular bifurcation formed by a junction of a branch vessel with a main vessel. As described more fully below, the apparatus 10 includes a balloon catheter 12 that is particularly useful in delivering and deploying a stent at or adjacent a bifurcation in a blood vessel. The apparatus 10 of the invention may be used with any conventional balloon catheter delivery system, including an over-the-wire balloon system or a rapid exchange balloon system. In addition, the apparatus 10 may be used to deploy any conventional balloon-deployable stent. Therefore, the scope of the present invention should not be limited to the exemplary delivery system and stents discussed below.

Figure 1:
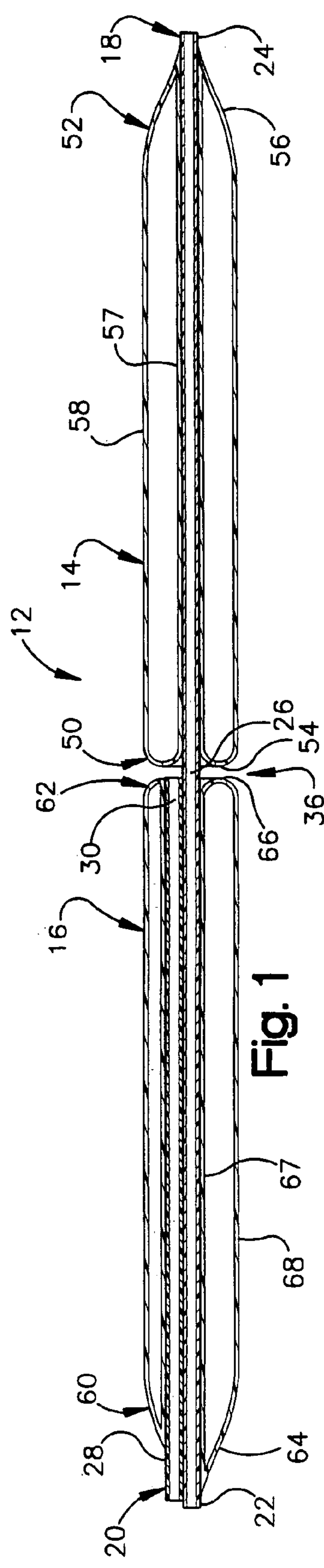
FIG. 1 is a schematic sectional view of a balloon catheter of an apparatus constructed in accordance with the present invention.

FIG. 1 illustrates the balloon catheter 12 of the apparatus 10. The balloon catheter 12 has first and second balloon portions 14 and 16, respectively. Each of the first and second balloon portions 14 and 16 is made of a conventional material, such as a polyolefin copolymer. The balloon catheter 12 also includes primary and secondary shafts 18 and 20, respectively. The shafts 18 and 20 may be made of any suitable material, such as polyethylene. The primary shaft 18 has oppositely disposed proximal and distal ends 22 and 24, respectively. A central section 26 of the primary shaft 18 is interposed between the proximal and distal ends 22 and 24. The primary shaft 18 includes cylindrical inner and outer surfaces that extend between the proximal and distal ends 22 and 24. The inner surface of the primary shaft 18 defines a primary channel that extends completely through the primary shaft 18 from the proximal end 22 to the distal end 24.

The secondary shaft 20 of the balloon catheter 12 also has oppositely disposed proximal and distal ends 28 and 30, respectively. The secondary shaft 20 includes cylindrical inner and outer surfaces that extend between the proximal and distal ends 28 and 30. The inner surface defines a secondary channel that extends completely through the secondary shaft 20 from the proximal end 28 to the distal end 30. The secondary shaft 20 is positioned adjacent to the primary shaft 18 such that the primary and secondary channels extend in parallel. In the balloon catheter 12 of FIG. 1, the secondary shaft 20 has a length that is approximately one-half a length of the primary shaft 18. The proximal end 28 of the secondary shaft 20 adjoins the proximal end 22 of the primary shaft 18. The distal end 30 of the secondary shaft 20 adjoins the central section 26 of the primary shaft 18.

The first balloon portion 14 is secured and sealed relative to the outer surface of the primary shaft 18 by suitable means, such as heat bonding or an appropriate adhesive. The first balloon portion 14 extends between the distal end 24 of the primary shaft and the central section 26. The first balloon portion 14 terminates immediately adjacent to the distal end 30 of the secondary shaft 20.

The first balloon portion 14 includes opposite proximal and distal ends 50 and 52, respectively. The proximal end 50 has a generally toroidal shape that is defined by an arcuate end surface 54. The arcuate end surface 54 curves toward the distal end 30 of the secondary shaft 20 as it extends from an inner diametrical surface 57 of the first balloon portion 14 that is secured to the outer surface of the primary shaft 18 to a radial midpoint of the first balloon portion. The arcuate end surface 54 then curves away from the distal end 30 of the secondary shaft 20 as it extends from the radial midpoint of the first balloon portion 14 to an outer diametrical surface 58 of the first balloon portion. The distal end 52 of the first balloon portion 14 has a generally frustoconical shape that is defined by a tapering end surface 56.

The second balloon portion 16 is secured and sealed relative to the outer surfaces of the primary and secondary shafts 18 and 20 by suitable means, such as heat bonding or an appropriate adhesive. The second balloon portion 16 extends between the proximal end 22 of the primary shaft 18 and the central section 26 of the primary shaft. The second balloon portion 16 also extends between the proximal end 28 of the secondary shaft 20 and the distal end 30 of the secondary shaft.

The second balloon portion 16 also includes opposite proximal and distal ends 60 and 62, respectively. The proximal end 60 has a generally frustoconical shape that is defined by a tapering end surface 64. The distal end 62 of the first balloon portion 14 has a generally toroidal shape that is defined by an arcuate end surface 66. The arcuate end surface 66 curves toward the proximal end 50 of the first balloon portion 14 as it extends from an inner diametrical surface 67 of the second balloon portion that is secured to the outer surfaces of the primary and secondary shafts 18 and 20 to a radial midpoint of the second balloon portion. The arcuate end surface 66 then curves away from the proximal end 50 of the first balloon portion 14 as it extends from the radial midpoint of the second balloon portion 16 to an outer diametrical surface 68 of the second balloon portion.

An annular gap 36 is located between the first and second balloon portions 14 and 16 of the balloon catheter 12. Specifically, the annular gap 36 is located between the proximal end 50 of the first balloon portion 14 and the distal end 60 of the second balloon portion 16. The arcuate end surfaces 54 and 66 function to minimize an axial length of the annular gap 36. Minimizing the axial length of the annular gap 36 helps to ensure complete and proper expansion the stent 40.

The annular gap 36, between the outer surface of the central section 26 of the primary shaft 18 and the outer diametrical surfaces of the first and second balloon portions 14 and 16, has a generally hourglass shape. Specifically, the annular gap 36 widens at a location near the outer surface of the central section 26 of the primary shaft 18 and at a location near the outer diametrical surfaces of the first and second balloon portions 14 and 16. The width of the annular gap 36 at the radially outermost location, i.e., located between the outer diametrical surfaces 58 and 68 of the first and second balloon portions 14 and 16, is equal to or less than the width of the annular gap at the radially innermost location adjacent the primary and secondary shafts, i.e., near the outer surface of the central section 26 of the primary shaft 18. A narrowest, axial length portion of the annular gap 36 is located between the radial midpoints of the first and second balloon portions 14 and 16.

Figure 5:
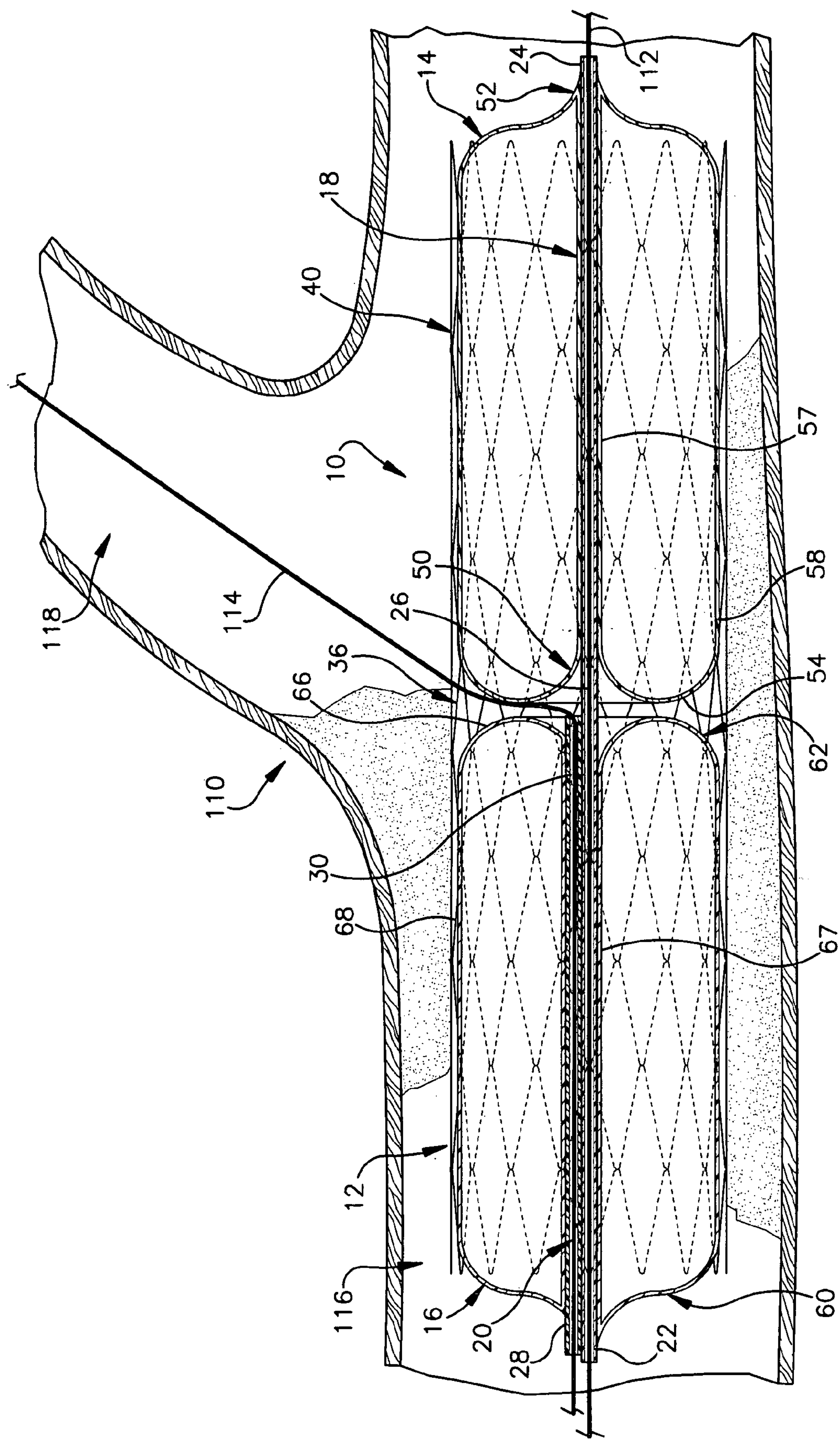
FIG. 5 is a schematic sectional view of the apparatus delivered to the bifurcation with the balloon portions of the balloon catheter in an inflated condition and the stent in an expanded condition.

In other words, the hourglass shape (when present) may be described with reference to a height of the annular gap measured radially between the radially outermost and radially innermost locations, as shown in FIG. 5. This "gap height" (unnumbered here, but extending substantially transverse to the gap width) may be larger than a longitudinal axial length of the annular gap measured at a radial midpoint of the first and second balloon portions. Under this descriptive scheme, the relationship between the gap height and the axial length of the annular gap measured at the radial midpoint of the first and second balloon portions provides the annular gap with a shape that one of ordinary skill in the art will recognize as a generally "hourglass" shape.

The apparatus 10 may also include one or more inflation tubes (not shown) located adjacent the shafts 18 and 20 and fluidly connected with one or both of the balloon portions 14 and 16. The inflation tubes are connectable with an inflation fluid source (not shown) for inflating of the first and second balloon portions 14 and 16. Alternatively, it is contemplated that the primary and secondary shafts 18 and 20 may be used to direct inflation fluid for inflating one or both of the first and second balloon portions 14 and 16. When the primary and secondary shafts 18 and 20 are used to direct inflation fluid for inflating one or both of the first and second balloon portions 14 and 16, openings (not shown), which communicate with the interior of the first and second balloon portions 14 and 16, may be added along the length of the primary and secondary shafts 18 and 20. It should be understood that, with any of the aforementioned inflation schemes, the first and second balloon portions 14 and 16 could be inflated at the same rate, pressure, and time or at different rates, pressures, and times.

Figure 2:
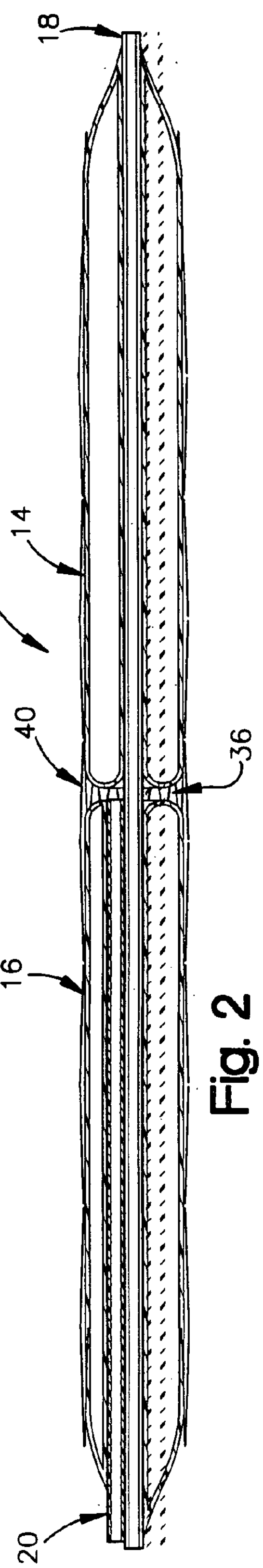
FIG. 2 is a view of the apparatus including the balloon catheter of FIG. 1 and an expandable stent.

FIG. 2 illustrates an expandable stent 40 of the apparatus 10 mounted on the balloon catheter 12. FIG. 2 illustrates the stent 40 in an unexpanded condition. Inflation of the first and second balloon portions 14 and 16 of the balloon catheter 12 expands the stent from the unexpanded condition to an expanded condition. Thus, the balloon catheter 12 is used for delivering and deploying the expandable stent 40. The stent 40 may have any conventional balloon-expandable configuration that is used to treat an atherosclerotic condition of a blood vessel, such as an occlusion or lesion that is caused by, for example, a stenosis or restenosis of the vessel. The stent 40 also may be a drug-eluting or a drug-coated stent, both which are known to help prevent restenosis following implantation of the stent.

Figure 3:
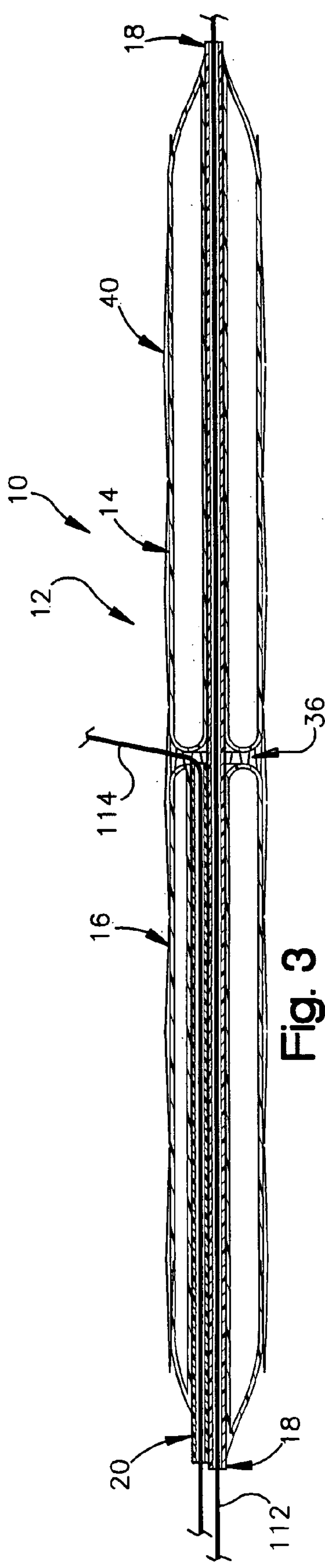
FIG. 3 is a view similar to FIG. 2 showing the apparatus placed over two guidewires for delivery to a bifurcation.

As shown in FIG. 3, the balloon catheter 12 of the apparatus 10 is designed for use with a pair of guidewires 112 and 114 in order to treat an occlusion occurring at or near a vascular bifurcation. As previously mentioned with reference to FIG. 7, the first guidewire 112 is positioned in the main vessel and the second guidewire 114 is positioned in the branch vessel of the bifurcation. During use of the apparatus 10, the first guidewire 112 is received in the primary channel of the primary shaft 18 and the second guidewire 114 is received in the secondary channel of the secondary shaft 20. The second guide wire 114 exits the balloon catheter 12 through the annular gap 36 located between the first and second balloon portions 14 and 16.

Figure 4:
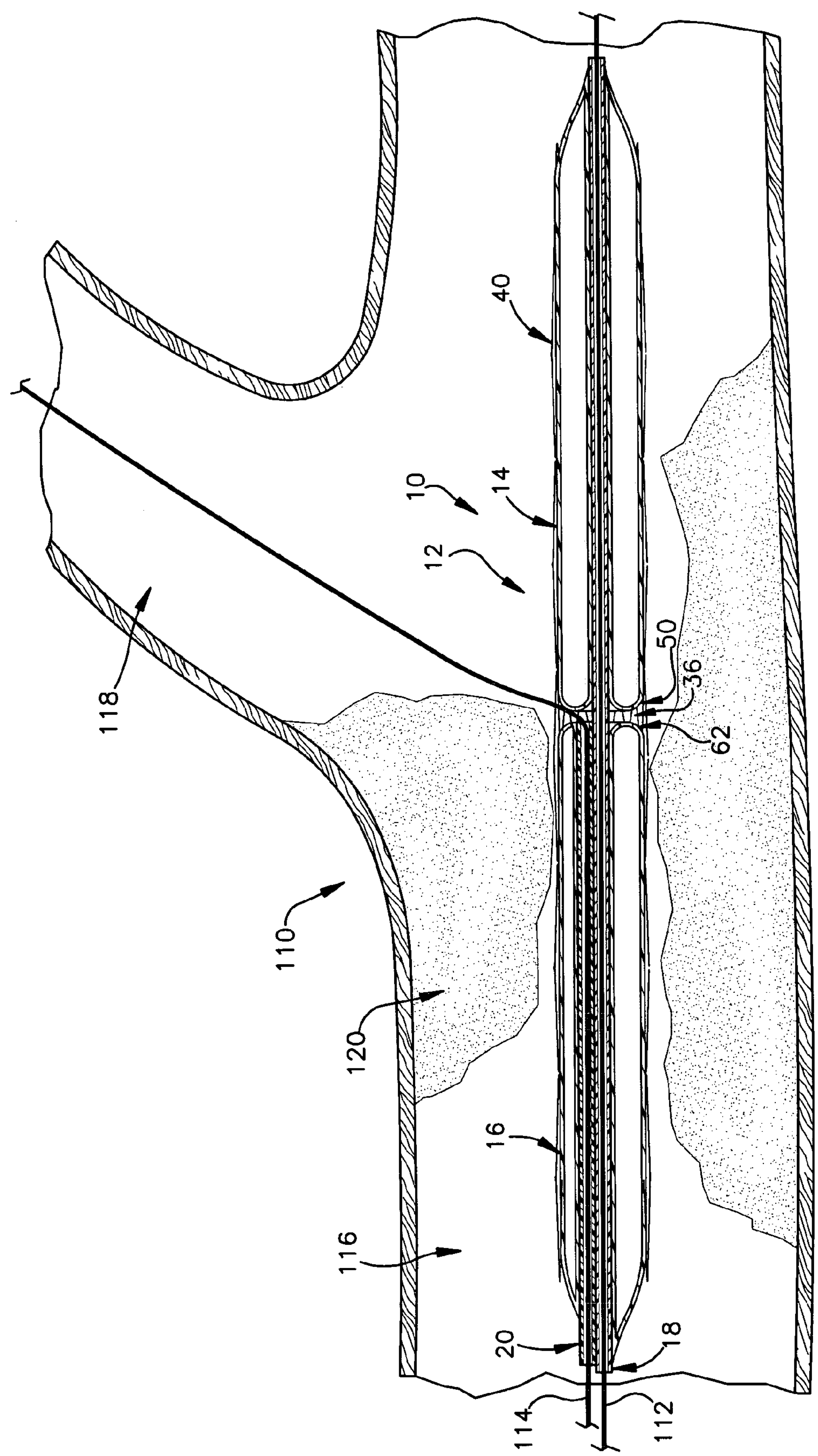
FIG. 4 is a schematic sectional view similar to FIG. 3 showing the apparatus delivered to the bifurcation with balloon portions of the balloon catheter in a non-inflated condition and the stent in an unexpanded condition.
Figure 7:
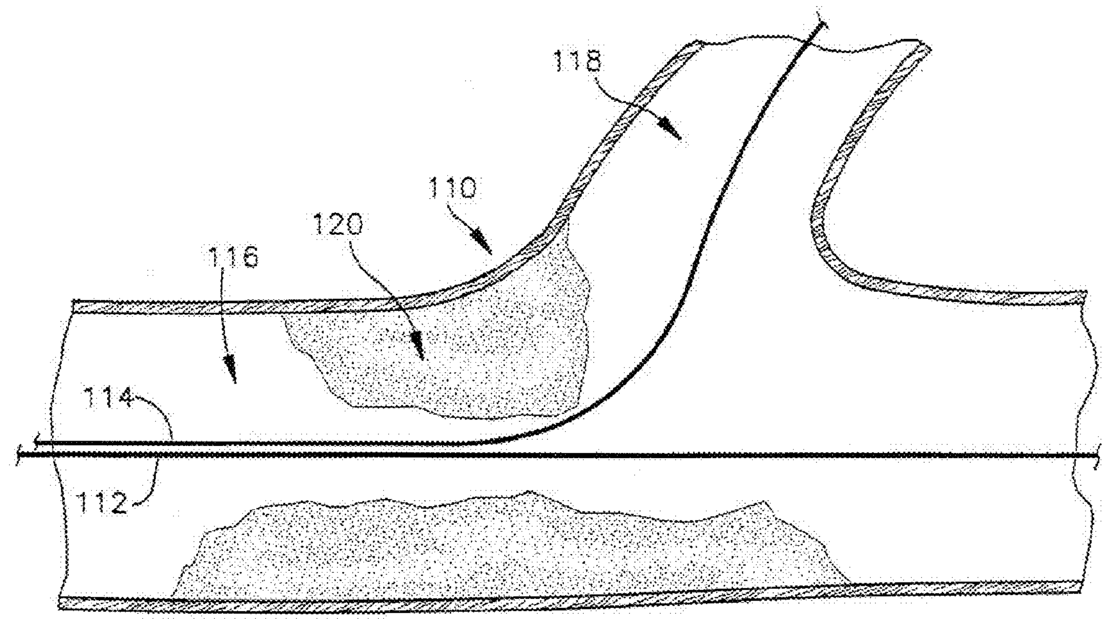
FIG. 7 is a schematic sectional view of a vascular bifurcation with a pair of guidewires placed across the bifurcation.
Figure 8:
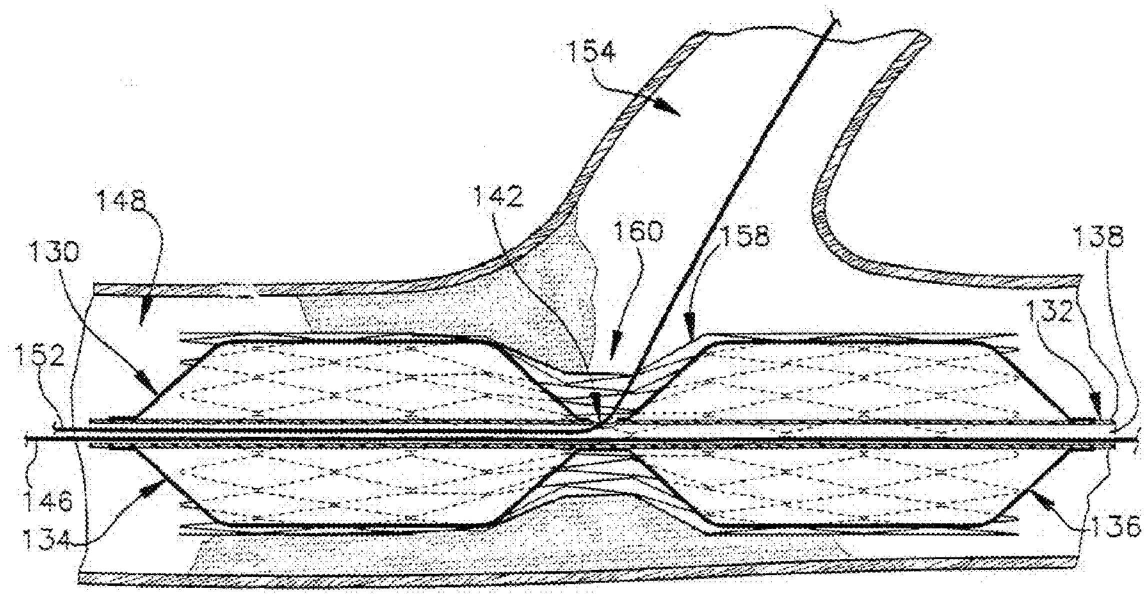
FIG. 8 schematically illustrates a prior art segmented balloon catheter with a mounted stent at a vascular bifurcation.

FIG. 4 illustrates the apparatus 10 of the present invention delivered to the bifurcation 110 previously described with reference to FIG. 7. When delivered to the bifurcation 110, the apparatus 10 is located in the main vessel 116. FIG. 4 illustrates the apparatus 10 in a delivered position spanning the opening of the branch vessel 118. The apparatus 10 alternatively may be located in the main vessel 116 adjacent the bifurcation 110 of the main vessel and the branch vessel 118. Also, prior to delivery of the apparatus 10, the occlusion 120 may be pre-dilated in a known manner, such as by using an angioplasty balloon.

The apparatus 10 is delivered to the bifurcation 110 along the first and second guidewires 112 and 114. As set forth above, the first guidewire 112 extends through the primary channel of the primary shaft 18 and the second guidewire 114 extends through the annular gap 36 between the first and second balloon portions 14 and 16 and into the secondary channel of the secondary shaft 20. The separation of the first and second guidewires 112 and 114 into the primary and secondary channels in the primary and secondary shafts 18 and 20, respectively, prevents tangling of the guidewires during insertion and delivery of the apparatus 10. By extending through the annular gap 36 between the first and second balloon portions 14 and 16, the second guidewire 114 helps to position the balloon catheter 12 of the apparatus 10 in the main vessel 116 across the opening to the branch vessel 118.

To deploy the stent 40 of the apparatus 10, the first and second balloon portions 14 and 16 are inflated. During inflation of the first and second balloon portions 14 and 16, the stent 40 expands into engagement with the main vessel 116 at the bifurcation 110 to help prevent atherosclerosis. FIG. 5 illustrates the apparatus 10 at the bifurcation 110 with the first and second balloon portions 14 and 16 of the balloon catheter 12 in an inflated condition and with the stent 40 in an expanded condition. One advantage recognized by the apparatus 10 of the present invention over prior art devices is that the stent 40 is uniformly expanded along its axial length, as FIG. 5 illustrates. Uniform expansion of the stent 40 occurs as a result of the narrow gap 36 formed between the adjacent ends 50 and 62 of the first and second balloon portions 14 and 16, respectively. After the stent 40 is fully deployed, the first and second balloon portions 14 and 16 may be deflated and removed from the main vessel 116.

As shown in FIG. 5, the second guidewire 114 extends radially outwardly through the expanded stent 40 and remains in the branch vessel 118 to provide access for additional intervention in the branch vessel as needed. For example, if necessary, a second stent (not shown) may be implanted in the branch vessel 118. This may be accomplished by threading another balloon catheter (not shown) having the second stent mounted thereon onto the second guidewire 114. The second balloon catheter may be similar to the balloon catheter 12 or may be any conventional balloon catheter. Similarly, the second stent may be similar to the stent 40 or may be another known balloon expandable stent. The second balloon catheter is then delivered to the bifurcation 110, passed radially through the stent 40 and into the branch vessel 118, and is inflated to expand the second stent into its deployed condition in the branch vessel. The second balloon catheter then may be deflated and removed. The second stent may be positioned such that a portion of the second stent is located at the intersection of the main vessel 116 and the branch vessel 118 to ensure that any occlusion which may exist at the intersection will be suitably engaged by the two stents.

Figure 6:
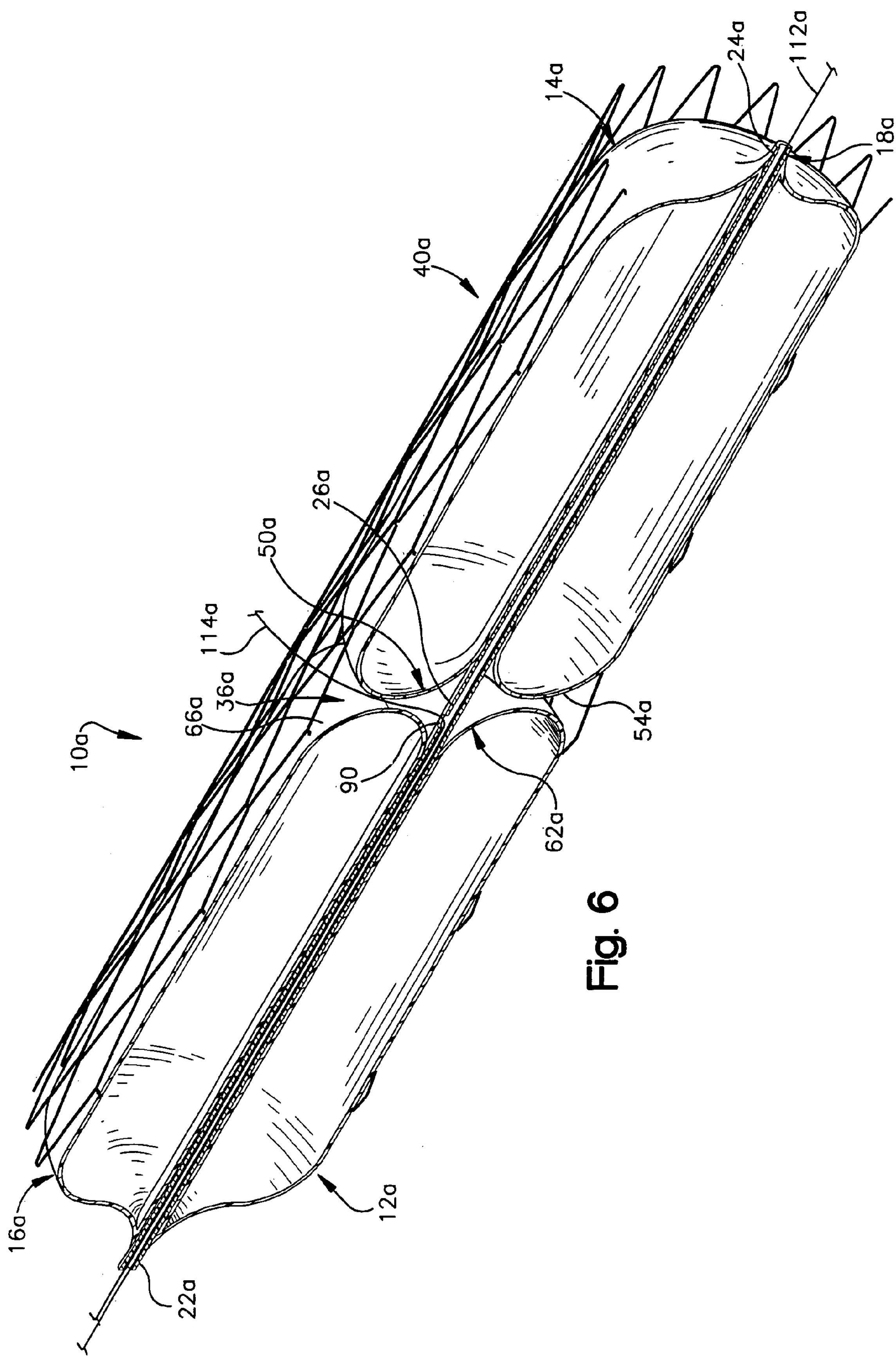
FIG. 6 is a schematic perspective view, in section, of an apparatus constructed in accordance with a second embodiment of the present invention.

FIG. 6 illustrates an apparatus 10*a* for interventional treatment of atherosclerosis at a vascular bifurcation in accordance with a second embodiment of the present invention. In FIG. 6, features that are the same as or similar to the features described with reference to the embodiments of FIGS. 1-5 are labeled using the same reference numbers with the addition of the suffix "a".

According to the embodiment of FIG. 6, the apparatus 10 comprises a balloon catheter 12*a* that includes first and second balloon portions 14*a* and 16*a*. The difference between the embodiment of FIG. 6 and the embodiment of FIGS. 1-5 is that the secondary shaft 20 has been eliminated in the embodiment of FIG. 6. As a result, both the first and second guidewires 112*a* and 114*a* are fed through the primary channel of the primary shaft 18*a*. Also, the primary shaft 18*a* of FIG. 6 includes an opening 90 in the central section 26*a*. The second guidewire 114*a* exits the primary channel of the primary shaft 18*a* through the opening 90.

The balloon catheter 12*a* of FIG. 6 functions in the same basic manner as the earlier described balloon catheter 12 to treat atherosclerosis at a bifurcation. With the second guidewire 114*a* extending through the gap 36*a* between the first and second balloon portions 14*a* and 16*a*, the second guidewire 114*a* helps to position the first and second balloon portions in the main vessel across the opening of the branch vessel. Following expansion of the stent 40*a*, the second guidewire 114*a* remains extended radially through the stent 40*a* and remains in the branch vessel to provide access for additional intervention in the branch vessel, such as, for example, placement of a second stent (not shown) in the branch vessel.

From the above description of the invention, those skilled in the art will perceive improvements, changes and modifications. Such improvements, changes and modifications within the skill of the art are intended to be covered by the appended claims.

Having described the invention, we claim:

1. An apparatus for interventional treatment of atherosclerosis at a vascular bifurcation formed by a junction of a branch vessel and a main vessel, the apparatus comprising:

structure for receiving a first guidewire positioned in the main vessel and a second guidewire positioned in the branch vessel, an exit for the second guidewire located in a central section of the structure;

a first balloon portion secured to the structure so a proximal end is located adjacent the exit;

a second balloon portion secured to the structure so a distal end is located adjacent the exit on a side of the exit opposite the first balloon portion;

an annular gap defined longitudinally between the proximal end of the first balloon portion and the distal end of the second balloon portion, the annular gap at a radially outermost location relative to the structure having a longitudinal width that is equal to or less than a width of the annular gap at a radially innermost location relative to the structure, the radially outermost and radially innermost locations being radially separated by a gap height, the gap height being larger than a longitudinal axial length of the annular gap measured at a radial midpoint of the first and second balloon portions, the relationship between the gap height and the axial length of the annular gap measured at the radial midpoint of the first and second balloon portions providing the annular gap with a generally hourglass shape, the second guidewire being extendable through the annular gap; and an expandable stent mountable about the first and second balloon portions and expandable by the first and second balloon portions into engagement with the main vessel at the vascular bifurcation.

2. The apparatus of claim 1 wherein the proximal end of the first balloon portion includes an arcuate end surface and the distal end of the second balloon portion includes an arcuate end surface, the arcuate end surfaces of the first and second balloon portions extending toward one another to define the hourglass shape of the annular gap.

3. The apparatus of claim 2 wherein the arcuate end surface of the proximal end of the first balloon portion curves outwardly from an inner diametrical surface of the first balloon portion to an outer diametrical surface of the first balloon portion, the arcuate end surface of the distal end of the second balloon portion curves outwardly from an inner diametrical surface of the second balloon portion to an outer diametrical surface of the second balloon portion.

4. The apparatus of claim 2 wherein the proximal end of the first balloon portion has a toroidal shape defined by the arcuate end surface of the first balloon portion, the distal end of the second balloon portion having a toroidal shape defined by the arcuate end surface of the second balloon portion.

5. The apparatus of claim 1 wherein the structure includes primary and secondary shafts, the primary shaft receiving the first guidewire and the secondary shaft receiving the second guidewire, the exit being a distal end of the secondary shaft, the distal end of the secondary shaft being located adjacent a central section of the primary shaft.

6. The apparatus of claim 5 wherein the secondary shaft has a length that is approximately one-half a length of the primary shaft.

7. The apparatus of claim 1 wherein the structure is a single shaft for receiving the first and second guidewires, an opening in the central section forming the exit.

8. The apparatus of claim 1 wherein the first and second balloon portions are inflatable for expanding the expandable stent, the annular gap being sized such that expansion of the first and second balloon portions expands the expandable stent uniformly along its axial length.

9. An apparatus for interventional treatment of atherosclerosis at a vascular bifurcation formed by a junction of a branch vessel and a main vessel, the apparatus comprising:

structure for receiving a first guidewire positioned in the main vessel and a second guidewire positioned in the branch vessel, an exit for the second guidewire located in a central section of the structure;

a first balloon portion secured to the structure so a proximal end is located adjacent the exit, the proximal end of the first balloon portion having an arcuate end surface;

a second balloon portion secured to the structure so a distal end is located adjacent the exit on a side of the exit opposite the first balloon portion, the distal end of the second balloon portion also having an arcuate end surface;

the arcuate end surfaces of the first and second balloon portions extending toward one another and defining an annular gap therebetween through which the second guidewire is extendable, the second guidewire is extendable, the annular gap at a radially outermost location relative to the structure having a longitudinal width that is equal to or less than a width of the annular gap at a radially innermost location relative to the structure, the radially outermost and radially innermost locations being radially separated by a gap height, the gap height being larger than a longitudinal axial length of the annular gap measured at a radial midpoint of the first and second balloon portions, the relationship between the gap height and the axial length of the annular gap measured at the radial midpoint of the first and second balloon portions providing the annular gap with a generally hourglass shape; and an expandable stent mountable about the first and second balloon portions and expandable by the first and second balloon portions into engagement with the main vessel at the vascular bifurcation.

10. The apparatus of claim 9 wherein the arcuate end surface of the proximal end of the first balloon portion curves outwardly from an inner diametrical surface of the first balloon portion to an outer diametrical surface of the first balloon portion, the arcuate end surface of the distal end of the second balloon portion curves outwardly from an inner diametrical surface of the second balloon portion to an outer diametrical surface of the second balloon portion.

11. The apparatus of claim 10 wherein the proximal end of the first balloon portion has a toroidal shape defined by the arcuate end surface of the first balloon portion, the distal end of the second balloon portion having a toroidal shape defined by the arcuate end surface of the second balloon portion.

12. The apparatus of claim 9 wherein the structure includes primary and secondary shafts, the primary shaft receiving the first guidewire and the secondary shaft receiving the second guidewire, the exit being a distal end of the secondary shaft, the distal end of the secondary shaft being located adjacent a central section of the primary shaft.

13. The apparatus of claim 12 wherein the secondary shaft has a length that is approximately one-half a length of the primary shaft.

14. The apparatus of claim 9 wherein the structure is a single shaft for receiving the first and second guidewires, an opening in the central section forming the exit.

15. The apparatus of claim 9 wherein the first and second balloon portions are inflatable for expanding the expandable stent, the annular gap being sized such that expansion of the first and second balloon portions expands the expandable stent uniformly along its axial length.

16. An apparatus for interventional treatment of atherosclerosis at a vascular bifurcation formed by a junction of a branch vessel and a main vessel, the apparatus comprising:

longitudinally oriented structure for receiving a first guidewire for positioning in the main vessel and a second guidewire for positioning in the branch vessel, an exit for the second guidewire located in a longitudinally central section of the structure;

a first balloon portion secured to the structure so a proximal end is located longitudinally adjacent the exit;

a second balloon portion secured to the structure so a distal end is located longitudinally adjacent the exit on a side of the exit longitudinally opposite the first balloon portion;

an annular gap defined longitudinally between the proximal end of the first balloon portion and the distal end of the second balloon portion, the annular gap at a radially outermost location relative to the structure having a longitudinal width that is equal to or less than a longitudinal width of the annular gap at a radially innermost location relative to the structure, the radially outermost and radially innermost locations being radially separated by a gap height, the gap height being larger than a longitudinal axial length of the annular gap measured at a radial midpoint of the first and second balloon portions, the relationship between the gap height and the axial length of the annular gap measured at the radial midpoint of the first and second balloon portions providing the annular gap with a generally hourglass shape, the second guidewire being extendable through the annular gap; and an expandable stent mountable about the first and second balloon portions and radially expandable by the first and second balloon portions into engagement with the main vessel at the vascular bifurcation.

17. The apparatus of claim 16 wherein the first and second balloon portions are inflatable for expanding the expandable stent, the annular gap being sized such that expansion of the first and second balloon portions radially expands the expandable stent uniformly along its axial length.

* * * * *